United States Patent

Van Egmond et al.

[11] Patent Number: 5,869,094
[45] Date of Patent: Feb. 9, 1999

[54] SOLID FORM OF ADMINISTRATION OF ISOSORBIDE 5-MONONITRATE

[75] Inventors: Cornelia Alida Maria Van Egmond, Haarlem; André Pullen, Zwanenburg; Sibo Wytse De Jong, Haarlem; Adrianus Petrus De Jong, Driehuis; Jan Bron, Giessenburg, all of Netherlands

[73] Assignee: BYK Gulden Lomberg Chemische Fabrik GmbH, Constance, Germany

[21] Appl. No.: 788,295

[22] Filed: Jan. 24, 1997

Related U.S. Application Data

[63] Continuation of Ser. No. 537,686, filed as PCT/EP94/01268, Apr. 28, 1994, abandoned.

[30] Foreign Application Priority Data

Apr. 27, 1993 [DE] Germany .......................... 43 13 726.1

[51] Int. Cl.$^6$ .............. A61K 9/50; A61K 31/34
[52] U.S. Cl. .......................... 424/451; 424/463; 424/465; 424/470; 424/474; 424/493; 424/497; 424/498; 514/964; 514/965
[58] Field of Search ...................... 424/451, 463, 424/465, 470, 474, 493, 497, 498; 514/964, 965

[56] References Cited

U.S. PATENT DOCUMENTS

| | | | |
|---|---|---|---|
| 4,812,316 | 3/1989 | Rossi et al. | 424/468 |
| 4,828,840 | 5/1989 | Sakamoto et al. | 424/474 |
| 5,149,542 | 9/1992 | Valducci | 424/493 |

*Primary Examiner*—Frederick Krass
*Attorney, Agent, or Firm*—Jacobson, Price, Holman & Stern, PLLC

[57] ABSTRACT

A solid form of oral administration of isosorbide 5-mononitrate with a controlled, pH-independent release of the active substance in the gastro-intestinal tract is constituted by a pellet coated with a depot layer and a release prolonging lacquer layer. The lacquer layer contains ethyl cellulose and polymethacrylate in a weight ratio from 3:1 to 3:2. The new form of administration is characterized in that it is less costly to produce.

3 Claims, No Drawings

SOLID FORM OF ADMINISTRATION OF ISOSORBIDE 5-MONONITRATE

RELATED APPLICATION

This application is a continuation of application Ser. No. 08/537,686, filed Jan. 4, 1995, now abandoned which is a 371 of PCT/EP 94/01268 Apr. 28, 1994.

AREA OF TECHNOLOGY

The invention relates to a solid form of isosorbide 5-mononitrate (IMN) for oral administration, with controlled pH-independent release of the active ingredient in the gastrointestinal tract, said form of administration comprising pellets coated with a depot layer (containing active ingredient) and a coating layer, with the coating layer serving to retard the rate of release.

STATE OF THE ART

The vasodilator isosorbide 5-mononitrate has found wide use in the treatment of cardiovascular disorders. Similar to other organic nitrates, IMN can give rise to undesirable side effects, such as cephalalgia, enlargement of skin blood vessels, and dizziness. These side effects are particularly likely if blood levels of the a.i. rise too rapidly after administration and/or reach excessive levels. Accordingly, various slow release means have been proposed for administering IMN.

In EP-A 0,163,000, a form of administration of IMN was described wherein a core is coated with four successive layers an isolating layer, a layer containing a.i., a coating layer, and a layer releasing an initial dose. The release of the initial dose is rapid, and the remainder of the a.i. is released over 9–10 hr. However, the manufacturing process needed is time-consuming and requires intensive monitoring.

In EP-A 0,202,051, the manufacture of gelatin capsules containing pellets was described. The pellets are produced by extrusion of a mixture of microcrystalline cellulose swellable in non-aqueous systems and the active ingredient. In order to achieve the desired release characteristics, it is necessary to produce three different types of pellet—uncoated, having a single coating, and having a double coating. The capsules are then filled with pellets of different types in a prescribed ratio. Thus, the manufacturing process involves numerous operations.

EP-A 0,396,425 discloses another form of administration based on pellets having different release characteristics. EP-A 0,219,161 describes the manufacture of tablets containing IMN [lit., "isosorbite 5-mononitrate" (sic)], wherewith polyvinyl pyrrolidone is present in order to increase stability. In PCT Patent App. WO 92/01446, granulates for readily soluble active ingredients are described which have a sub-coating of wax or a waxy polymer to block outward diffusion of the a.i.

DESCRIPTION OF THE INVENTION

The underlying problem of the invention is to devise a solid form of IMN for oral administration, having a release characteristic which is controlled and is pH-independent, providing bioequivalence at least equal to that of the forms of administration presently on the market, and capable of being produced in a relatively large batch [sic] process which is completely automated and has appreciably fewer [lit., "the lowest possible number of"] process steps compared to known methods.

This problem is solved by a form of administration wherein the coating layer contains ethylcellulose and polymethacrylate (Eudragit® RS-100) in a ratio of 3:1 to 3:2 by weight. The principal claimed matter of the invention is a solid form of IMN for oral administration, with controlled pH-independent release of the active ingredient in the gastrointestinal tract, said form of administration comprising pellets coated with a depot layer and a coating layer, with the coating layer serving to retard the rate of release; characterized in that the said coating layer contains ethylcellulose and polymethacrylate (Eudragit® RS-100) in a ratio in the range of 3:1 to 3:2 by weight.

Other features of the invention are set forth in the claims.

It is particularly preferred for the weight ratio of ethylcellulose and polymethacrylate (Eudragit® RS-100) to be 2:1. The usual softening agents for the coating layer may be used; particularly preferred is the plasticizer dibutyl phthalate. The depot layer contains hydroxypropyl methylcellulose and polyvinyl pyrrolidone in a weight ratio in the range from 2:1 to 1:2, preferably about 1:1. It is advantageous if polyethylene glycol is also used in the production of the depot layer.

It is known to one skilled in the art to provide active ingredients in a depot layer applied to inert sugar spherules by means of spray-application of an organic and/or aqueous solution or suspension. When the known method is used for IMN, one observes either after the application of the depot layer or after storage for a certain time that the spherules have a non-uniform surface. This is attributable to the fact that IMN tends to crystallize out of the coating solution or -suspension. This crystallization leads to release behavior which is no longer controllable. It has been discovered that, surprisingly, this problem can be solved by simple means if one applies the entire amount of the IMN in a part of the coating solution, e.g. half of the amount of the said coating solution or -suspension, immediately followed by application of the remaining amount of the coating solution or -suspension (not containing IMN). In a preferred embodiment of the inventive method, a mixture of ethanol, demineralized water, hydroxypropyl methylcellulose, polyvinyl pyrrolidone, talc, and polyethylene glycol is prepared, and all of the IMN which is to be applied is dissolved in a 45% portion of this mixture. Then the inert sugar spherules are coated with the active-ingredient-containing part of the suspension, followed by coating with the part not containing the a.i., in a single process unit-operation. The resulting spherules release the a.i. completely and rapidly at the pH of the stomach (1.2) and [sic] that of the duodenum (7.4). The spherules containing a.i. are then coated with a coating which leads to pH-independent controlled release. Under the circumstances presented, the state of the art would dictate use of ethylcellulose for this coating; and such a coating would indeed provide pH-independent release. However, the release would be too rapid. In order to achieve the desired release profile, a disproportionately large amount of ethylcellulose would be needed, which would be costly in that it would lengthen the manufacturing time. Attempts to use coatings comprised of various types of polymethacrylates which the manufacturers literature describes as being suitable for producing coatings which provide pH-independent release have not given the desired release profile. Surprisingly, coating membranes can be produced which lead to a reproducible, pH-independent release profile if one employs coating solutions which contain ethylcellulose, polymethacrylate, and a plasticizer. A particularly suitable ethylcellulose is Ethocel® 10 cps [viscosity] (Dow Chemical Company). Eudragit® RS-100 (Röhm Pharma GmbH) has proven particularly suitable as a polymethacrylate. The ratio of ethylcellulose to polymethacrylate in the coating solution or -suspension is advantageously in the range 3:1 to 3:2 by weight, preferably 2:1. The preferred plasticizer is dibutyl phthalate. The coating components as applied are preferably dissolved in acetone in the presence of demineralized water. No special requirements apply to the apparatus used for applying the depot layer and the layer providing the controlled release property. The coating may be applied using customary coating apparatus.

MANUFACTURING EXAMPLE

The following mixture was prepared for producing a depot layer:

| | |
|---|---|
| Ethanol | 7899 ml |
| Water, demineralized | 878 ml |
| Hydroxypropyl methylcellulose (pharmacoat ®, 3 cps) | 438.9 g |
| Polyvinyl pyrrolidone (Kollidone ® 25) | 438.9 g |
| Talc | 131.7 g |
| Polyethylene glycol (PEG 6000) | 43.9 g |

Approximately 787.8 g IMN (isosorbide 5-mononitrate) were dissolved in approximately 45 parts [by wt.] of this suspension. This concentrated suspension [portion], containing about 197.0 g polyvinyl pyrrolidone, 197.0 g hydroxypropyl methylcellulose, 59.1 g talc, and 19.7 g polyethylene glycol, was sprayed onto 1158.6 g inert sugar spherules of diameter 0.5–0.6 mm. Such spraying may be carried out in the customary apparatus therefor, e.g. a fluidized bed coater with a dryer, preferably containing a rotor. Immediately after this spraying, the remaining suspension (55 parts [by wt.]), not containing active ingredient but containing approximately the following:

241.9 g hydroxypropyl methylcellulose, 241.9 g polyvinyl pyrrolidone, 72.6 g talc, and 24.2 g polyethylene glycol was applied. The resulting pellets had a surface which appeared smooth under a microscope and which released IMN rapidly.

These pellets were coated with the following solution [which is free from fatty acids containing from 12 to 20 carbons and/or paraffin (USP XXI, page 1584)], to provide a retarding coat:

| | |
|---|---|
| Acetone | 497.0 g |
| Water demineralized | 33.3 g |
| Ethylcellulose (Ethocel ® 10 cps) | 33.3 g |
| Polymethyl methacrylate (Eudragit ® RS-100) | 16.7 g |
| Dibutyl phthalate | 5.0 g |
| Talc | 0.5 g |

The release of IMN from the final pellets was pH-independent and corresponded to that of approved products. Tests on volunteers showed that the inventive pellets are bioequivalent to approved products.

Thus, the product is the equivalent of approved preparations but can be manufactured at substantially lower cost.

We claim:

1. A method of manufacturing a solid form of isosorbide 5-mononitrate (IMN) for oral administration, with controlled pH-independent release of active ingredient in the gastrointestinal tract, said form of administration comprising pellets coated with a depot layer (containing the active ingredient) and a coating layer, with the coating layer serving to retard the rate of release; characterized in that, in a single unit-operation, a solution of IMN, in a part of an aqueous ethanolic suspension containing hydroxypropyl methylcellulose and polyvinyl pyrrolidone, is spray-coated onto inert sugar spherules, following which the remainder of the said suspension (not containing IMN) is applied, also by spray-coating, whereafter the resulting pellets containing active ingredient are sprayed with a solution containing as sole essential components, plasticizer, ethylcellulose and polymethacrylate.

2. A method of manufacturing a solid form of isosorbide-5-mononitrate (IMN) for oral administration, with controlled pH-independent release of active ingredient in the gastrointestinal tract, said form of administration comprising pellets coated with a depot layer (containing the active ingredient) and a coating layer, with the coating layer serving to retard the rate of release; characterized in that, in a single unit-operation, a part of a solution containing IMN is spray coated onto inert granules, following which the remainder of the solution (not containing IMN) is applied, also by spray coating, whereafter the resulting pellets containing the active ingredient are sprayed with a solution containing ethylcellulose and polymethacrylate.

3. A solid form of isosorbide-5-mononitrate (IMN) for oral administration prepared by the method of claim 2.

* * * * *